United States Patent [19]

Bubik

[11] Patent Number: 4,491,013

[45] Date of Patent: Jan. 1, 1985

[54] APPARATUS AND METHOD FOR HIGH PRESSURE TESTING AND INSPECTION OF TIRES

[76] Inventor: Leslie M. Bubik, 421 Roselawn Ave., Toronto, Ontario, Canada

[21] Appl. No.: 485,231

[22] Filed: Apr. 15, 1983

[51] Int. Cl.³ .................... G01M 17/02; G01N 29/04
[52] U.S. Cl. ........................................ 73/146; 73/592; 73/40.5 A
[58] Field of Search ................ 73/146, 146.2, 592, 73/649, 618, 40.5 A; 340/58

[56] References Cited

U.S. PATENT DOCUMENTS

| | | | |
|---|---|---|---|
| 2,695,520 | 11/1954 | Karsai | 73/146 |
| 3,336,794 | 8/1967 | Wysoczanski et al. | 73/618 |
| 4,275,589 | 6/1981 | Dugger et al. | 73/618 |

*Primary Examiner*—Donald O. Woodiel
*Attorney, Agent, or Firm*—Niro, Jager & Scavone

[57] ABSTRACT

A method and apparatus are disclosed for inspecting and testing tires under high pressure in excess of 50 p.s.i. The apparatus includes a base, a pair of flanges on the shaft which support the tire, means for moving the flanges together to insure a seal between the flanges and the tire beads and means for introducing air under pressure into the interior of the tire. High frequency sound wave sensing means and indication means are also provided.

14 Claims, 6 Drawing Figures

APPARATUS AND METHOD FOR HIGH PRESSURE TESTING AND INSPECTION OF TIRES

BACKGROUND OF THE INVENTION

The present invention relates to the tire service equipment industry and more particularly to an apparatus and method for testing and inspecting tires under high pressure. The invention finds its principal application in the field of tire retreading and repair and is useful in the inspection and testing of tire casings prior to retreading or repair and of finished tires after the retread or repair has been completed.

It is well known in the art that a tire may be inspected or tested for defects, such as ply separations and nail holes, or for quality control of finished, repaired or retreaded tires when fully or partially inflated. However, when a tire is inflated to high pressure, i.e. in excess of 50 p.s.i., defects may be more pronounced or more efficiently detected than when the tire is not inflated. Nevertheless, high pressure inspection and testing of tires is relatively uncommon because of the time required to mount the tire, inflate it and then remove the tire from the wheel after the inspection or test procedure has been completed. In addition, prior art equipment designed to facilitate high presure tire servicing has been relatively complex and expensive and has found only limited acceptance in the tire retreading and repair industry.

One common and troublesome defect found in used tires that would otherwise be suitable for retreading and repair is the difficulty associated with discovering and locating small air leaks, such as nailholes. A variety of non-destructive testing devices have been suggested in the art for solving this problem, including high voltage electronic discharge machines and several different forms of ultrasonic testing apparatus.

For the most part, the nail hole detection equipment of the prior art utilizes non-inflated tires. A few prior art devices have used inflated tires. In either case, however, the prior art equipment all suffers from the disadvantage that it is costly, complex equipment and oftentimes difficult to use.

SUMMARY OF THE INVENTION

The present invention is directed to both an apparatus and method for the high pressure inspection and testing of tires. The term "high pressure" as used in this specification and in the appended claims is intended to mean internal tire pressure in excess of about 50 p.s.i. and up to more than 100 p.s.i.

The apparatus of the present invention includes a base, a shaft extending from the base, first and second flanges slidably and rotatably mounted on the shaft, means for holding the flanges on the shaft, means for moving one or both flanges along the shaft to seal the beads of a tire against the peripheral seats of each flange, and means for introducing air under pressure into the tire to inflate the tire to in excess of 50 p.s.i. Other embodiments of the apparatus of the present invention includes one or more sensors capable of receiving high frequency sound waves generated by air escaping from the highly pressurized tire, and an indicator associated with each sensor which gives a visual or aural signal upon reception of such sound waves by the sensor.

The method of the present invention comprises the steps of loosely mounting a tire on a pair of flanges having peripheral seals capable of sealing against the tire beads, compressing the tire between the flanges until a seal has been effected between each flange and the respective opposing beads of the tire, introducing air under pressure into the interior of the tire while simultaneously moving the flanges apart to the extent necessary to permit the tire to assume a generally normal operating configuration, and inspecting or testing the highly pressurized tire for defects.

BRIEF DESCRIPTION OF THE DRAWINGS

The novel and patentable features of the present invention are set forth in the appended claims. However, the structure, function, operation and advantages of the invention will be better understood by reference to the following description in conjunction with the accompanying drawings, in which:

DETAILED DESCRIPTION OF THE PREFERRED EMBODIMENTS

Figure 1:
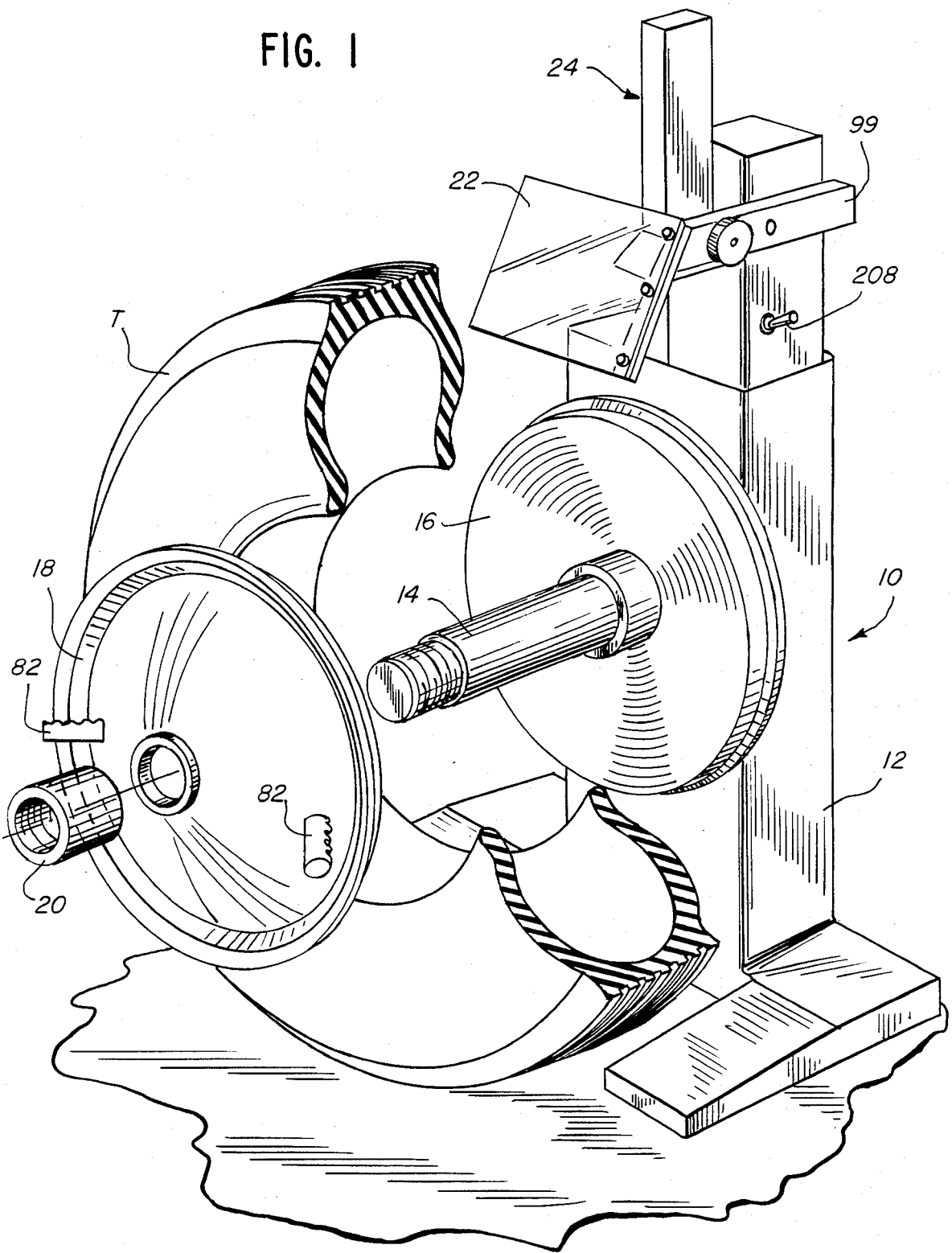
FIG. 1 is an exploded perspective view, in partial cross-section, illustrating one preferred form of the apparatus of the present invention.
Figure 2:
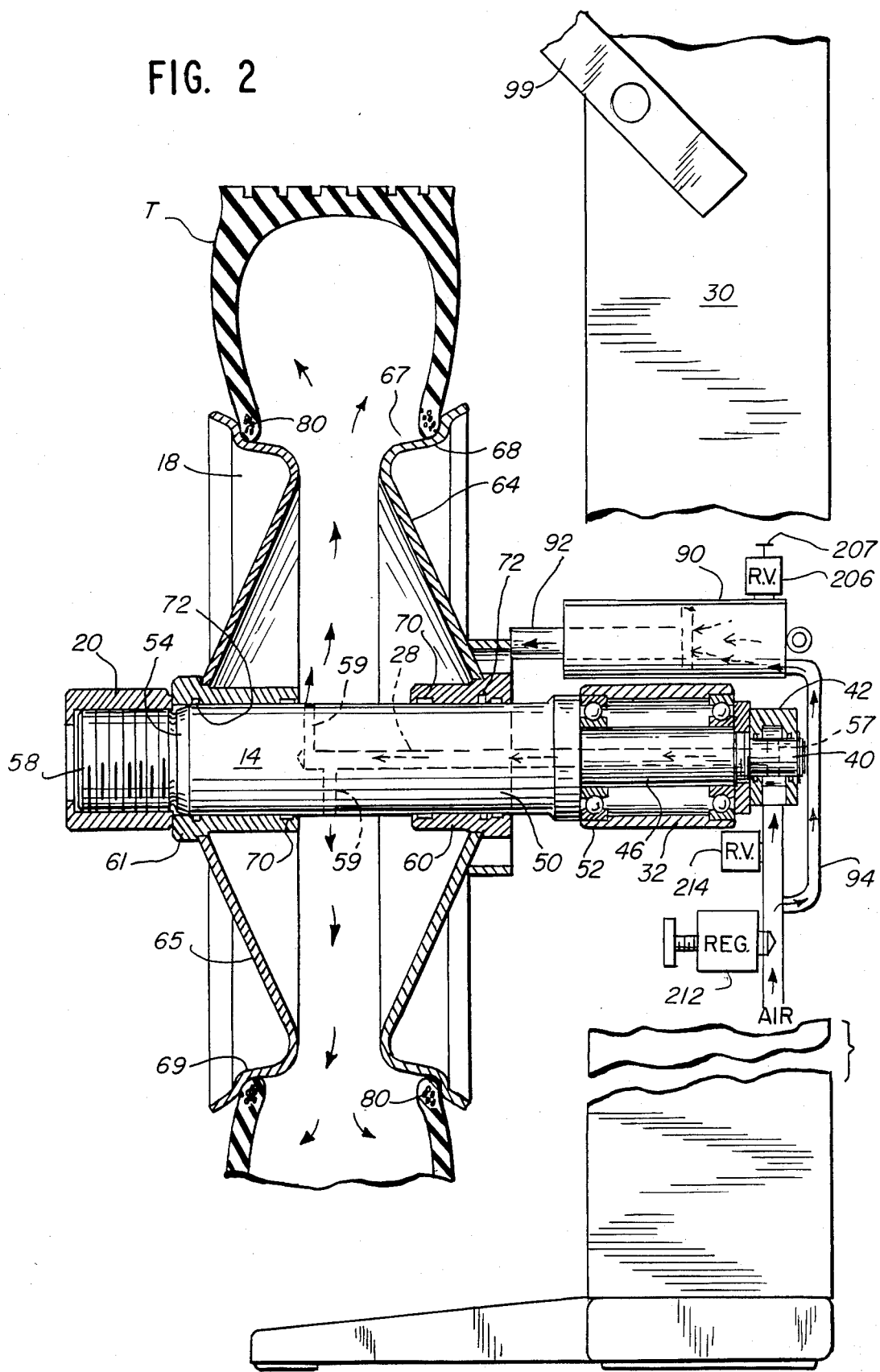
FIG. 2 is a side elevational view, in partial cross-section, illustrating the apparatus of FIG. 1 in the initial bead sealing position at the beginning of the tire pressurizing cycle.

Referring to FIGS. 1 and 2 of the drawings, the apparatus of the present invention for use with tire T is designated generally as 10, and includes a base 12, shaft 14, flanges 16 and 18, stop means 20, shield 22 and leak detecting means 24. Further elements of the apparatus 10 include flange moving means 26 and means for introducing air into the interior of the tire comprising air passageway 28.

The base 12 is constructed with an upstanding support member 30 from which the shaft 14 extends in cantilever fashion. Support member 30 also houses a main bearing 32 which permits and facilitates rotation of the shaft.

Figure 3:
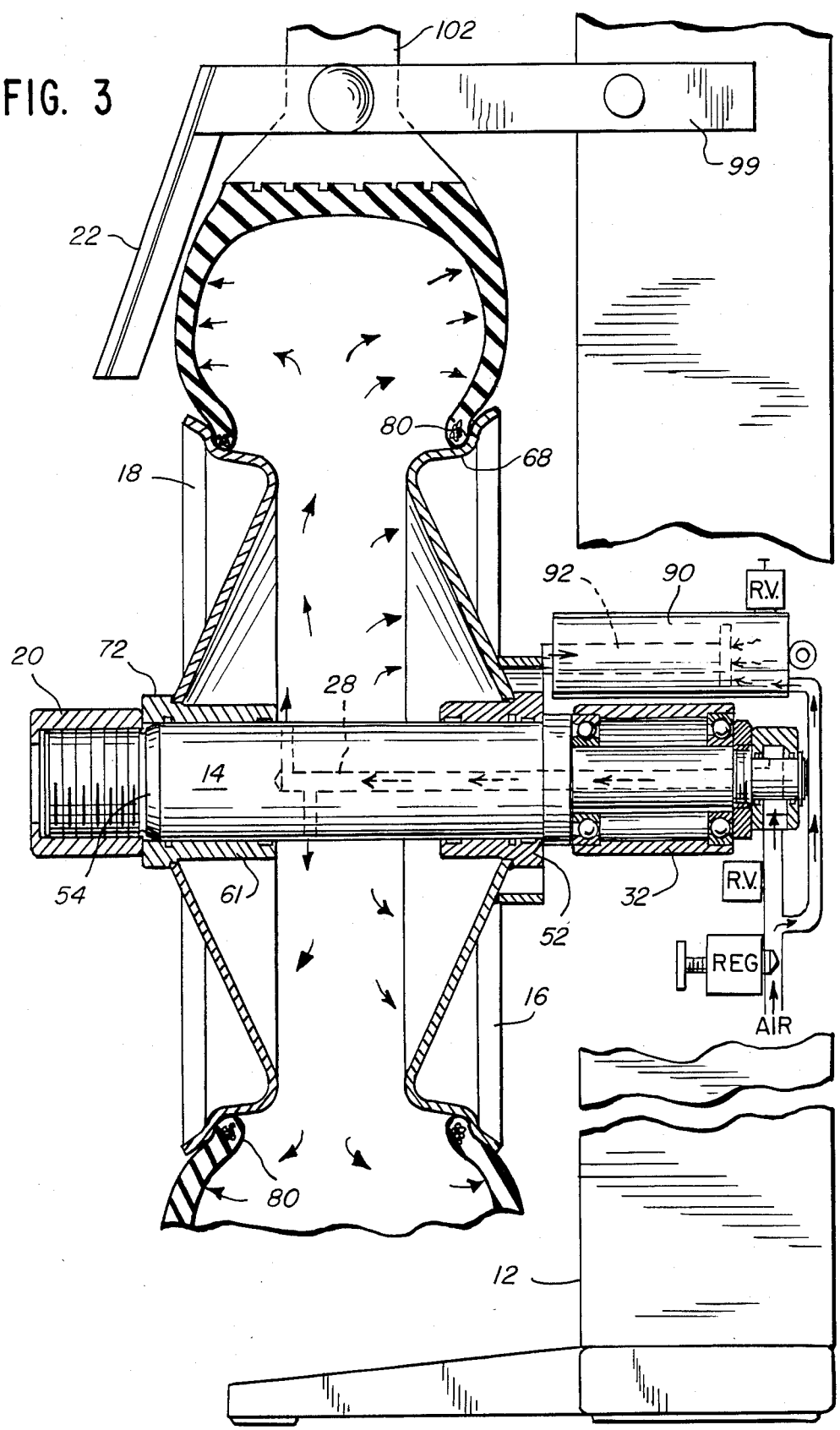
FIG. 3 is a side elevational view similar to that of FIG. 2, but showing the tire fully pressurized and with the apparatus shield and leak sensing apparatus in operating position adjacent the pressurized tire.

As is most clearly seen in FIGS. 2 and 3, shaft 14 includes a series of different sections. At its base is a reduced end portion 40 which rotates within a stationary air manifold 42. The shaft also includes a journal section 46 which rotates within main bearing 32. Extending from support member 30 is the flange mounting section 50 which begins at shoulder 52 and terminates at the tapered neck 54. Finally, shaft 14 includes a threaded free end 58 on which the stop means, nut 20, is threaded. The air passageway 28 extends as a longitudinal bore from the end section 40 into the flange mounting section 50 and includes input ports 57 which communicate with air manifold 42 and discharge ports 59 which are positioned intermediate the two flanges.

The flanges 16 and 18 include central hubs 60 and 61 respectively, conical bodies 64 and 65, and peripheral seats 68 and 69. The hubs are designed to have a sliding fit over section 50 of the shaft and incorporate conventional wear rings 70 and air tight seals, such at O-rings 72. The peripheral seats 68 and 69 are configured to seal against the beads 80 of the tire, and at least flange 16 includes a relatively wide shoulder 67, at least 1 inch and preferably 1½ inches in width, which facilitates mounting the tire T. Flange 16 ordinarily remains on the shaft 14 while flange 18 must be mounted and removed from the shaft in the normal use of the apparatus. Handles 82 are provided on flange 18 for this purpose. Moreover, the flanges can be manufactured from steel by various well known processes which limit their weight to about 20–40 pounds which also allows for convenient handling.

Flange moving means 26 comprises an assembly of cylinder 90 and piston 92 of conventional design which is pneumatically powered and supplied via air passageway 94 from the same source of high pressure air as is air passageway 28. The free end of piston 92 aligns with hub 60, and when extended by virtue of air pressure within cylinder 90, it drives flange 16 toward flange 18, thereby compressing the tire and effecting a seal between peripheral seats 68 and 69 and the tire beads 80.

The apparatus of the present invention is also provided with a safety shield 22 which can be fabricated from any one of a variety of well known transparent and shatter resistant plastics. The shield 22 is mounted in a fashion to permit movement from a position remote from the mounted tire T to an operative position adjacent the tire. For example, as shown in FIGS. 2 and 3, shield 22 may be carried by an arm 99 which is pivotally mounted to support member 30.

Finally, apparatus 10 includes means 24 for detecting and locating small air leaks, such as nail holes, in tire T. The leak detecting means includes at least one and preferably a plurality of sensor means 100 capable of receiving high frequency sound waves generated by air escaping from the tire while under high pressure. As used in this specification and in the appended claims, the term "high frequency sound waves" is intended to mean sound waves having a frequency above that generally audible to the human ear, i.e. above about 20 KHZ. Thus, the sensor means 100 are adapted to receive sound waves above 20 KHZ and to thereby differentiate these high frequency sound waves from background noise in the tire retread or repair shop environment. It has been found that such sensor devices should preferably exhibit receptivity of sound waves in the range of about 30 to 50 KHZ, and a variety of such devices or "ultrasonic receivers" are well known and available in the market. One such receiver found suitable in the practice of the present invention is marketed by American Gas & Chemical Company, Ltd, 220 Pegasus Ave., Northvale, N.J. 07647, under the trade name SONIC 3000.

Indicator means, such as lights 101 or sound emitter 103 or both, are associated with each sensor 100 and each transmits a visual or aural signal in response to the sensor's reception of high frequency sound waves generated by air escaping from the tire. Such indicators and the associated electronic hardware are very well known to those skilled in the art and are available in various forms, such as small incandescent lamps, light emitting diodes and electronic horns or buzzers.

Figure 4:
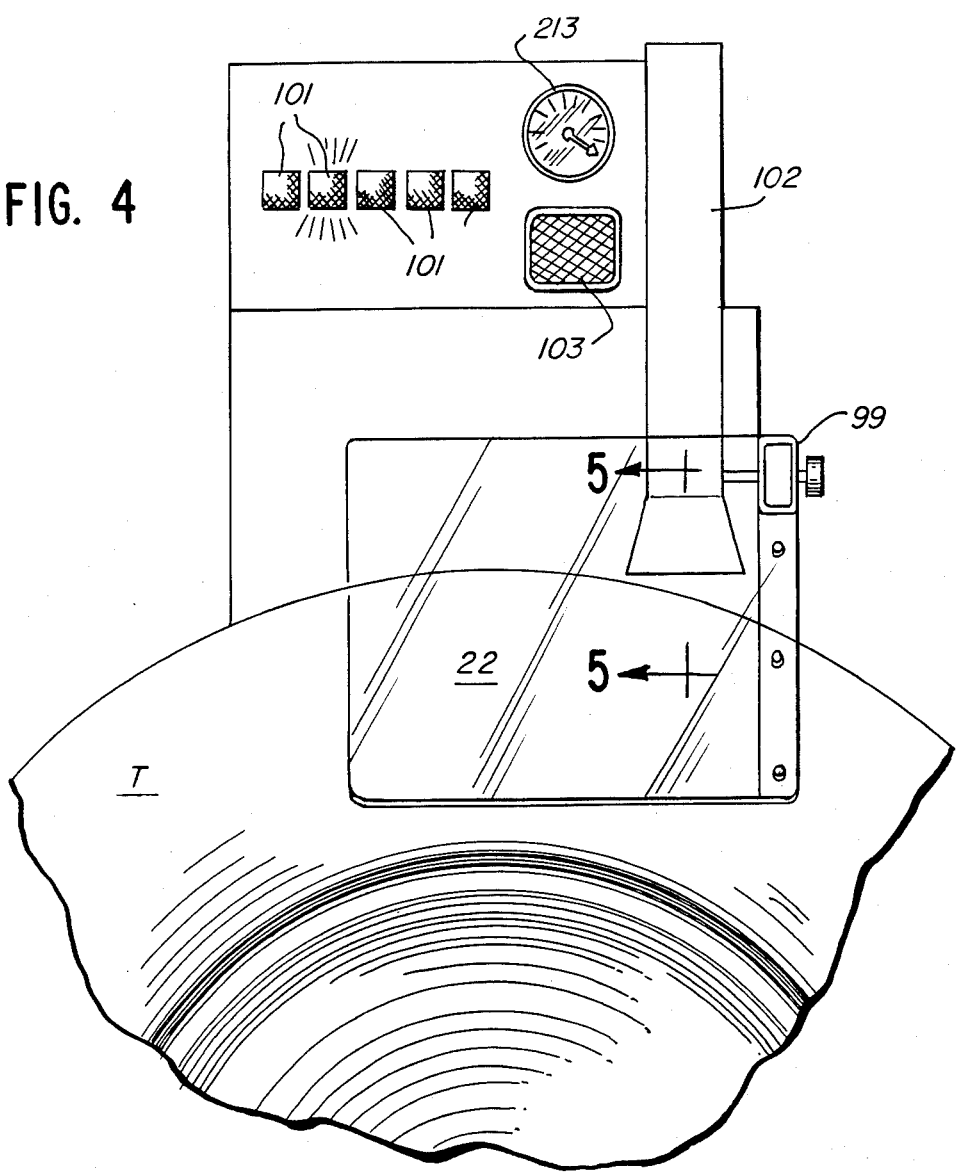
FIG. 4 is a partial front view of one form of the apparatus of the present invention and showing a preferred leak sensing and indicator means in operation.
Figure 5:
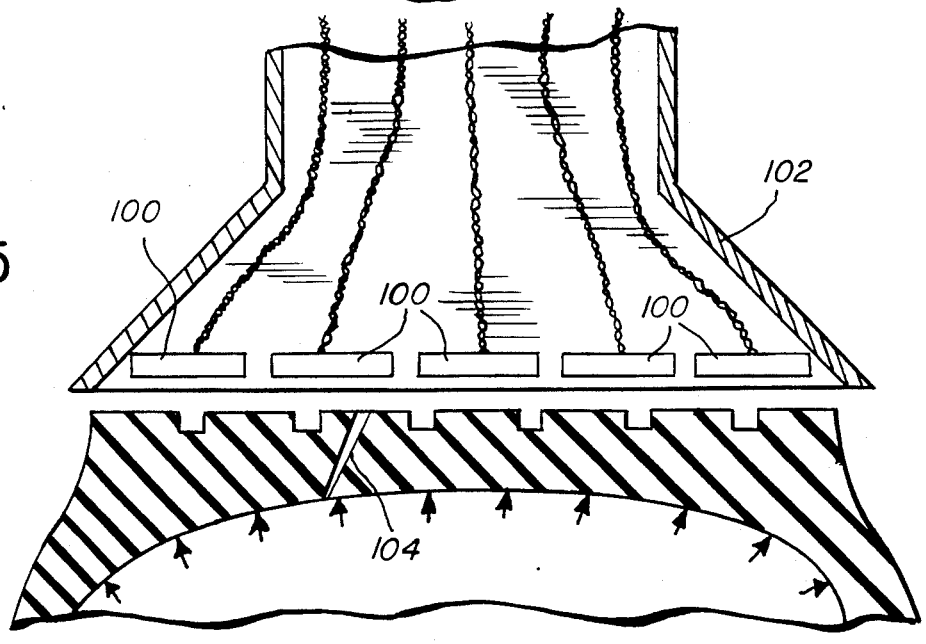
FIG. 5 is an enlarged cross-sectional view taken along line 5—5 of FIG. 4.

The sensors 100 are preferably mounted in a line generally transverse to or across the tread of tire T and relatively close to the thread. A spacing of about ½ to 1½ inches from the surface of the tire has been founded suitable when using about five sensors, as shown in FIG. 5. Also it is preferable that the sensors 100 be positioned within a housing 102 which serves to protect against mechanical damage and to isolate a limited circumferential area of the tire for "inspection" by the sensors. Thus, a tire defect which permits escape of air from the highly pressurized tire, such as nail hole 104, will only be detected while within the confines of the hood walls. In this manner the circumferential location of the defect may be determined, and high frequency sound waves generated by other defects, if any, will not interfere with the leak locating process. In addition, the use of a plurality of sensors across the tread and a like number of indicators, as shown in FIG. 4 will permit both circumferential and transverse or lateral location of the defect simultaneously.

Like the shield 22, the leak detecting means 24 may be mounted to arm 99 and is movable between a position remote from the tire to an operating position adjacent the tire.

Figure 6:
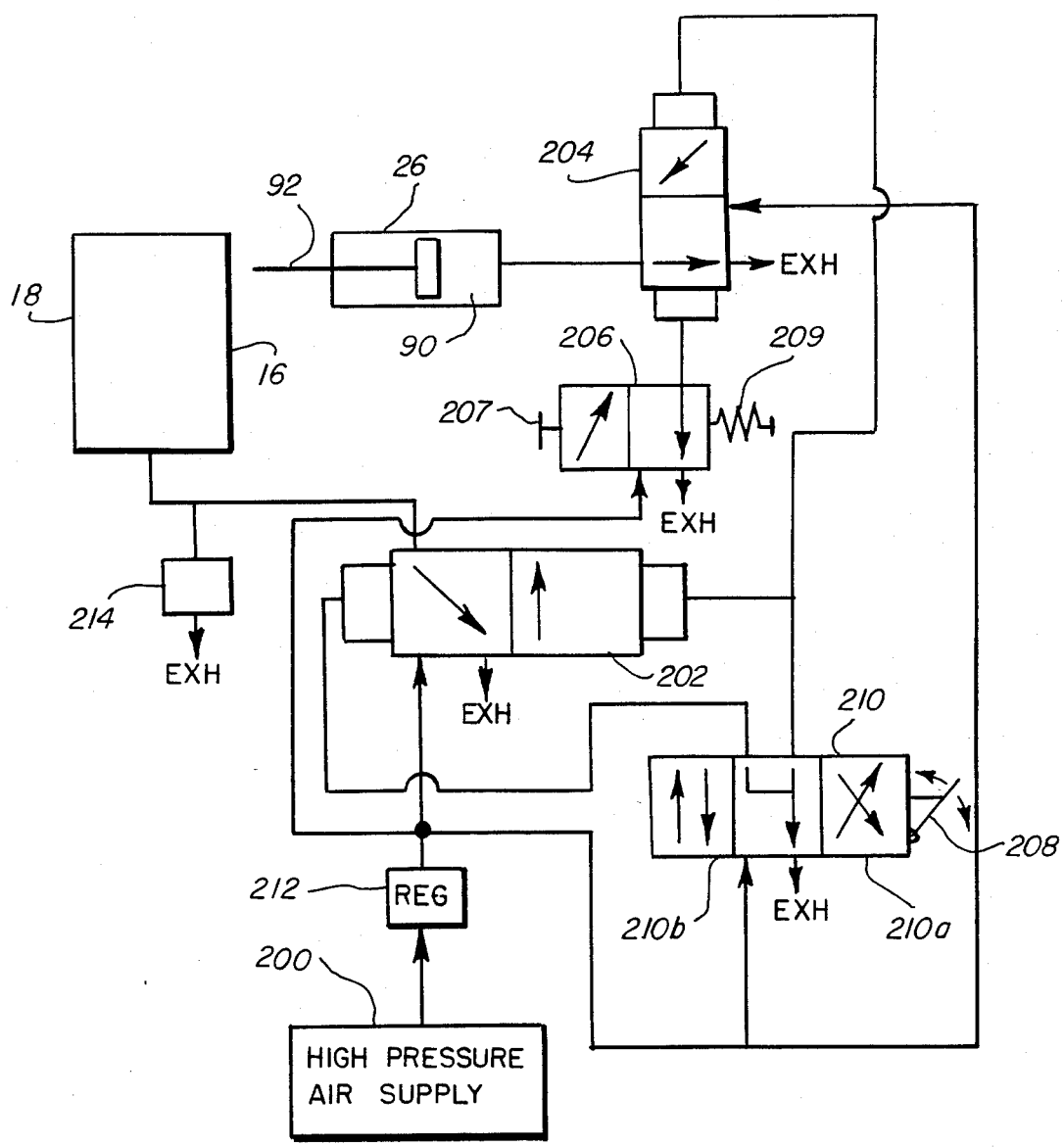
FIG. 6 is a schematic view illustrating a pneumatic circuit suitable for use in the present invention.

While a variety of pneumatic, fluidic, hydraulic or electronic controls may be employed to operate apparatus 10, one preferred pneumatic circuit is shown schematically in FIG. 6. The circuit includes a high pressure air supply 200, a pair of two-way, high volume air valves 202 and 204, a manually activated relief valve 206 and a three-way pilot valve 210 which is activated by toggle switch 208.

When the circuitry is in the "off" mode all valves are in the exhaust position as shown in FIG. 6. After a tire has been mounted on flanges 16 and 18, the toggle switch is moved to actuate the pilot valve to position 210a which will convert the circuit to the "inflation" mode wherein both valves 202 and 204 are opened and high pressure air enters the flange-tire assembly and flange moving means 26. After inflation, the pressure within cylinder 90 may be released by manually depressing button 207 against the bias of spring 209. Finally, in order to convert the circuit to the "discharge" mode, the toggle is moved to actuate the pilot valve to position 210b wherein both valves 202 and 204 will exhaust to atmosphere. A regulator 212 and automatic relief valve 214 may also be included in the system.

In the operation of apparatus 10 in accord with the method of the present invention. A tire T is first placed with one bead resting on shoulder 67 of flange 16 and the second flange 18 is slid over the free end of shaft 14 and onto flange mounting section 50 of the shaft. Next the stop nut 20 is threaded completely onto the end of the shaft. At this point, the tire beads 80 may or may not be sealed against flange seats 68 and 69.

After assembly on the flanges and tire on shaft 14 a supply of high pressure air is opened to passageways 28 and 98 by means of pivot valve 210, through toggle switch 208. The system pressure will have been preset by pressure regulator 212 and can be monitored by pressure gauge 213. As the apparatus reaches operating pressure, i.e. in excess of 50 p.s.i. and preferably about 65 p.s.i., flange moving means 26, specifically piston 92, moves flange 16 toward flange 18 to effect a complete seal between the flange seats and the tire beads. At this point air discharging through ports 59 will inflate the tire to operating pressure, and, because the area of flange 16 is greater than that of piston 92, flange 16 will move along shaft section 50 until hub 60 abuts shoulder 52. As a result, tire T will inflate and expand to a generally normal operating configuration. Moreover, the entire force generated by inflation of the tire is balanced between stop nut 20 and shoulder 52, and no force is transmitted to bearing 32 which is free to rotate without interference. This arrangement permits easy manual rotation of the tire while inflated.

It should be noted that the tapered neck 54 provides a safety feature which prevents pressurizing the tire when stop nut 20 is not properly threaded into shaft 14. The O-ring 72 which seals the interior of the tire will not seat when positioned over the tapered neck. As a result, if the stop nut 20 is not completely threaded onto and section 58 of shaft 14, flange 18 will move to the left upon initial pressurization of the tire and internal pressure will be lost under O-ring 72.

At this point, if desired, the operator may manually depress button 96 which will release the pressure within cylinder 90. As a result, piston 92 will not exert any force against hub 60 and the tire, flange and shaft assembly will rotate freely on bearing 32. If, at a later time, it is necessary or desirable to lock the tire to prevent rotation, the operator simply reactivates the pilot valve 210 through toggle switch 208.

After the tire is fully inflated, it may be inspected, tested or repaired in a number of ways. For example, nail holes or other small defects may be located with the leak detection means simply by swinging arm 99 from its remote position (shown in FIG. 2) to its operating position with sensors 100 adjacent to the tire T and rotating the tire through one complete revolution. Any air escaping through such a small hole will generate high frequency sound waves which will, in turn, activate one of the indicators when received by the sensors.

The apparatus described herein is also well suited for other tire repairs and retreading operations well known to those skilled in the art such as buffing, tread stitching, and sidewall repairs such as those disclosed in U.S. Pat. No. 4,375,231.

It will be apparent to those skilled in the art that certain changes and modifications may be made in the apparatus and method of the present invention. The description of the preferred embodiments, therefore, are to be considered in all respects as illustrative and not restrictive with regard to the scope of the invention, and all such changes or modifications are intended to be covered by the appended claims.

I claim:

1. An apparatus for high pressure testing and inspection of a tire having opposing beads, said apparatus comprising:
    base;
    shaft extending from said base;
    first and second flanges slidably and rotatably mounted on said shaft, each including a peripheral seat designed to seal against one of said tire beads;
    stop means for holding said flanges on said shaft;
    means for moving one or both flanges along the shaft to reduce the space between said flanges and to seal the flange seats against the beads of a tire mounted on said flanges; and
    means for introducing air into the interior of said tire to pressurize the tire.

2. The apparatus of claim 1 wherein said flange moving means comprises a cylinder and piston assembly mounted in fixed position relative to said base and operatively associated with one of said flanges to move said one flange toward the other flange of said shaft.

3. The apparatus of claim 2 wherein said cylinder and piston assembly is pneumatically powered.

4. The apparatus of claim 1 wherein said flanges are adapted to override said flange moving means and to move along the shaft away from one another as said tire is pressurized.

5. The apparatus of claim 1 wherein said base includes an upstanding support member and said shaft is rotatably mounted on said support member and extends generally horizontally therefrom.

6. The apparatus on claim 5 wherein said base also includes a shield mounted on said support member and movable from a first position remote from a tire mounted on the flanges to a second, operating position adjacent to and covering a portion of said tire.

7. The apparatus of claim 1 wherein said air introducing means comprises a longitudinal bore within said shaft and one or more discharge ports located between said flanges on said shaft.

8. The apparatus of claim 1 wherein said flange moving means is pneumatically powered and both said flange moving means and said air introducing means are supplied by a common source of pressurized air.

9. The apparatus of claim 1 further including at least one sensor means positioned adjacent a pressurized tire mounted on said flanges for receiving high frequency sound waves generated by air escaping from said tire; and indicator means for transmitting an aural or visual signal upon reception of said high frequency sound waves by said sensor means, whereby the circumferential location of small air leaks in said tire may be determined.

10. The apparatus of claim 9 wherein a plurality of sensor means are positioned adjacent to and generally across the width of said tire, and wherein each said sensor means is associated with a separate indicator means, whereby both the circumferential and transverse location of small air leaks is said tire may be determined.

11. The apparatus of claim 9 wherein said sensor is disposed within a housing mounted on said base, said housing being movable from a first position remote from a tire mounted on the flanges to a second, operating position adjacent to said tire.

12. An apparatus for pressurizing and testing a tire having opposing beads, said apparatus comprising:
    base;
    means supported by said base for sealing said tire at its opposing beads;
    means for introducing air into the interior of said tire to pressurize the tire;
    at least one sensor means supported by said base and positioned adjacent the pressurized tire for receiving high frequency sound waves generated by air escaping from said tire; and
    indicator means for transmitting an aural or visual signal upon reception of said high frequency sound waves by said sensor means, whereby the circumferential and transverse location of small air leaks in said tire may be determined.

13. A method for high pressure testing or inspection of a tire having opposing beads, comprising the steps of:
    loosely mounting said tire on a pair of flanges having peripheral seats capable of sealing against said tire beads;

compressing the tire between said flanges until a seal has been effected between each flange and the respective opposing beads of the tire;

introducing air under pressure into the interior of the tire to pressurize the tire while simultaneously moving the flanges apart to the extent necessary to permit the pressurized tire to assume a generally normal operating configuration; and inspecting the surface of the tire with sensor means capable of detecting high frequency sound waves generated by air escaping from the tire to thereby determine the circumferential and transverse location the source of such escapting air.

14. The apparatus of claim 1 wherein said shaft is rotatably mounted on said base by means of a bearing, and the forces generated by the internal pressure of said tire are not transmitted to said bearing.

* * * * *